(12) United States Patent
Campbell et al.

(10) Patent No.: US 10,780,251 B2
(45) Date of Patent: Sep. 22, 2020

(54) EXPANDABLE MEDICAL DEVICES

(75) Inventors: Carey V. Campbell, Flagstaff, AZ (US); Joel M. Greene, Flagstaff, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1122 days.

(21) Appl. No.: 12/884,711

(22) Filed: Sep. 17, 2010

(65) Prior Publication Data

US 2012/0071912 A1 Mar. 22, 2012

(51) Int. Cl.
*A61M 25/10* (2013.01)
*A61F 2/958* (2013.01)

(52) U.S. Cl.
CPC ............. *A61M 25/10* (2013.01); *A61F 2/958* (2013.01); *A61M 2025/1081* (2013.01)

(58) Field of Classification Search
CPC ...... A61F 2002/9583; A61F 2002/9522; A61F 2/962; A61F 2/966; A61F 2002/9665; A61F 2/97; A61M 2025/1081; A61M 2025/1084; A61M 2025/1045
USPC .................. 606/191, 192; 623/1.11, 1.12, 1.2
See application file for complete search history.

(56) References Cited

U.S. PATENT DOCUMENTS

| | | | |
|---|---|---|---|
| 4,950,227 A * | 8/1990 | Savin et al. .................. | 623/1.12 |
| 5,108,416 A * | 4/1992 | Ryan ........................ | A61F 2/958 604/103.05 |
| 5,348,538 A * | 9/1994 | Wang et al. ............. | 604/103.12 |
| 5,403,341 A * | 4/1995 | Solar ........................ | A61F 2/86 606/198 |
| 5,409,495 A | 4/1995 | Osborn | |
| 5,445,646 A * | 8/1995 | Euteneuer ................ | A61F 2/95 604/103.02 |
| 5,470,313 A | 11/1995 | Crocker et al. | |
| 5,512,051 A | 4/1996 | Wang et al. | |
| 5,514,093 A * | 5/1996 | Ellis et al. ..................... | 604/103 |
| 5,545,209 A * | 8/1996 | Roberts .................... | A61F 2/958 604/103.05 |
| 5,549,551 A * | 8/1996 | Peacock, III ........... | A61F 2/958 604/103.05 |
| 5,549,635 A * | 8/1996 | Solar ........................ | A61F 2/86 606/198 |
| 5,653,689 A * | 8/1997 | Buelna et al. ........... | 604/103.09 |
| 5,676,654 A * | 10/1997 | Ellis et al. .................... | 604/103 |
| 5,738,653 A | 4/1998 | Pinchuk et al. | |
| 5,743,876 A | 4/1998 | Swanson | |
| 5,766,201 A * | 6/1998 | Ravenscroft ............ | A61F 2/958 606/108 |
| 5,807,398 A * | 9/1998 | Shaknovich .............. | A61F 2/01 606/194 |

(Continued)

FOREIGN PATENT DOCUMENTS

| WO | WO 2009005933 A1 * | 1/2009 | ............. A61M 25/10 |
|---|---|---|---|
| WO | WO 2009029674 A1 * | 3/2009 | ............. A61F 2/856 |

*Primary Examiner* — Darwin P Erezo
*Assistant Examiner* — Erin L Colello

(57) ABSTRACT

A medical device with an expandable element and slidable constraint of at least two portions surrounding the expandable element which slides away from the middle region and toward the distal and proximal ends of the expandable element upon expansion of the expandable element to influence the rate, shape and/or force required to expand the expandable element and methods for use in a body lumen are provided.

33 Claims, 10 Drawing Sheets

(56) References Cited

U.S. PATENT DOCUMENTS

| | | | |
|---|---|---|---|
| 5,843,092 A * | 12/1998 | Heller et al. | 606/108 |
| 5,843,116 A | 12/1998 | Crocker et al. | |
| 5,944,726 A * | 8/1999 | Blaeser et al. | 623/1.11 |
| 5,961,536 A * | 10/1999 | Mickley et al. | 606/194 |
| 5,980,530 A * | 11/1999 | Willard | A61F 2/958 606/195 |
| 6,068,634 A * | 5/2000 | Lorentzen Cornelius | A61F 2/958 606/198 |
| 6,120,477 A | 9/2000 | Campbell et al. | |
| 6,174,316 B1 * | 1/2001 | Tuckey et al. | 606/108 |
| 6,183,505 B1 * | 2/2001 | Mohn, Jr. | A61F 2/958 623/1.11 |
| 6,200,290 B1 | 3/2001 | Burgmeier | |
| 6,270,504 B1 * | 8/2001 | Lorentzen Cornelius | A61F 2/958 606/108 |
| 6,280,411 B1 * | 8/2001 | Lennox | 604/103.05 |
| 6,280,412 B1 * | 8/2001 | Pederson, Jr. | A61F 2/958 604/103.07 |
| 6,328,710 B1 | 12/2001 | Wang et al. | |
| 6,344,045 B1 * | 2/2002 | Lim | A61F 2/958 604/194 |
| 6,387,118 B1 * | 5/2002 | Hanson | A61F 2/958 623/1.11 |
| 6,391,032 B2 * | 5/2002 | Blaeser | A61F 2/958 606/108 |
| 6,428,506 B1 * | 8/2002 | Simhambhatla | A61L 27/16 428/36.9 |
| 6,432,080 B2 * | 8/2002 | Pederson, Jr. | 604/103.07 |
| 6,432,130 B1 * | 8/2002 | Hanson | A61F 2/958 606/194 |
| 6,478,814 B2 * | 11/2002 | Wang | A61F 2/958 623/1.12 |
| 6,517,548 B2 * | 2/2003 | Lorentzen Cornelius | A61F 2/958 606/108 |
| 6,565,595 B1 * | 5/2003 | DiCaprio | A61F 2/958 623/1.11 |
| 6,585,747 B1 * | 7/2003 | Limon | A61F 2/958 606/108 |
| 6,589,274 B2 * | 7/2003 | Stiger | A61F 2/958 606/192 |
| 6,607,552 B1 * | 8/2003 | Hanson | 623/1.11 |
| 6,726,714 B2 * | 4/2004 | DiCaprio | A61F 2/958 623/1.11 |
| 6,814,746 B2 * | 11/2004 | Thompson et al. | 623/1.11 |
| 6,830,575 B2 * | 12/2004 | Stenzel et al. | 606/108 |
| 6,866,649 B2 | 3/2005 | Ferrera et al. | |
| 6,890,395 B2 | 5/2005 | Simhambhatla | |
| 6,964,676 B1 * | 11/2005 | Gerberding | A61F 2/958 606/108 |
| 7,037,327 B2 * | 5/2006 | Salmon et al. | 623/1.11 |
| 7,048,713 B2 | 5/2006 | Wang | |
| 7,163,523 B2 | 1/2007 | Devens, Jr. et al. | |
| 7,226,472 B2 * | 6/2007 | Pederson, Jr. | A61F 2/958 623/1.11 |
| 7,314,476 B2 * | 1/2008 | Senzaki et al. | 606/194 |
| 7,717,953 B2 * | 5/2010 | Kaplan et al. | 623/1.35 |
| 8,114,049 B2 * | 2/2012 | Freyman et al. | 604/103.08 |
| 8,206,431 B2 * | 6/2012 | Seppala | A61F 2/958 606/108 |
| 8,333,795 B2 * | 12/2012 | Weber | A61F 2/856 604/103.07 |
| 9,370,647 B2 * | 6/2016 | Campbell | A61M 25/104 |
| 2001/0029378 A1 * | 10/2001 | Blaeser et al. | 606/108 |
| 2001/0032008 A1 * | 10/2001 | Wang | A61F 2/958 623/1.11 |
| 2002/0007207 A1 * | 1/2002 | Shin et al. | 623/1.11 |
| 2002/0029046 A1 * | 3/2002 | Lorentzen Cornelius | A61F 2/958 606/108 |
| 2002/0038141 A1 * | 3/2002 | Yang et al. | 623/1.12 |
| 2002/0072789 A1 * | 6/2002 | Hackett | A61F 2/958 623/1.12 |
| 2004/0049204 A1 * | 3/2004 | Harari | A61F 2/958 606/108 |
| 2006/0015064 A1 | 1/2006 | Kastenhofer | |
| 2006/0085058 A1 * | 4/2006 | Rosenthal | A61F 2/958 623/1.11 |
| 2008/0125707 A1 | 5/2008 | Wilson et al. | |
| 2008/0147182 A1 * | 6/2008 | Righini | A61F 2/243 623/2.11 |
| 2008/0167708 A1 * | 7/2008 | Molland et al. | 623/1.17 |
| 2008/0171977 A1 | 7/2008 | Blix | |
| 2009/0069878 A1 * | 3/2009 | Weber | A61F 2/856 623/1.11 |
| 2009/0076446 A1 | 3/2009 | Dubuclet, IV et al. | |
| 2009/0076584 A1 * | 3/2009 | Mao et al. | 623/1.11 |
| 2009/0137954 A1 | 5/2009 | Kastenhofer | |
| 2009/0163879 A1 * | 6/2009 | Weber | A61F 2/856 604/264 |
| 2009/0171277 A1 | 7/2009 | Pepper | |
| 2009/0227948 A1 * | 9/2009 | Chen | A61L 29/085 604/103.02 |
| 2010/0022949 A1 | 1/2010 | Eidenschink | |

* cited by examiner

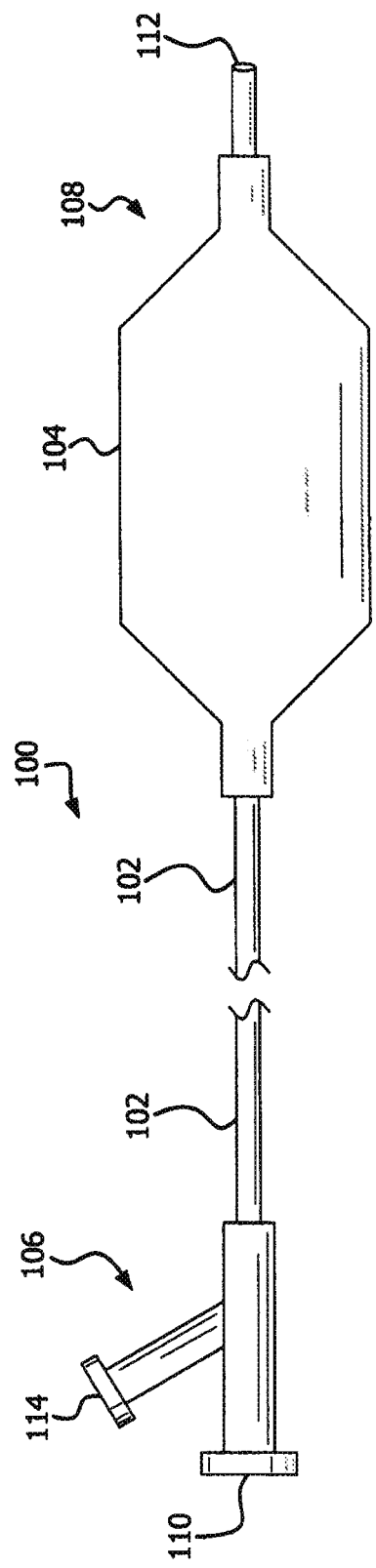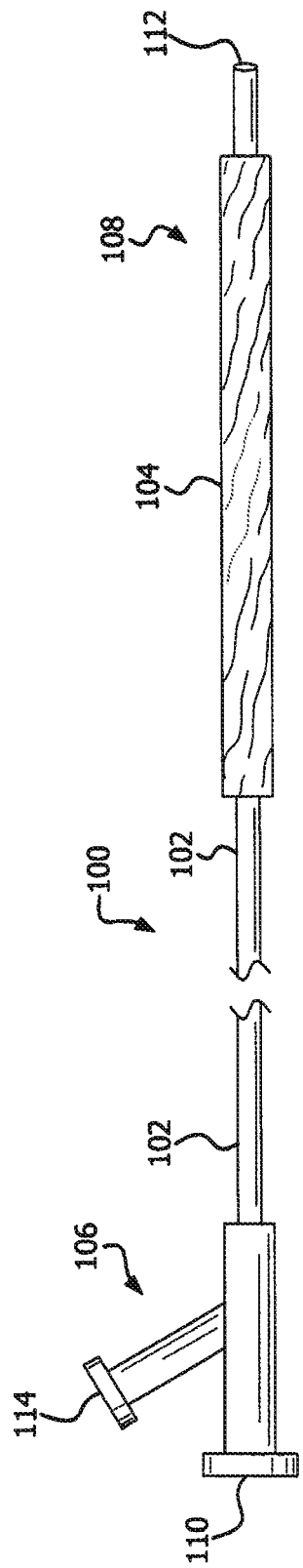
FIG. 1
FIG. 2

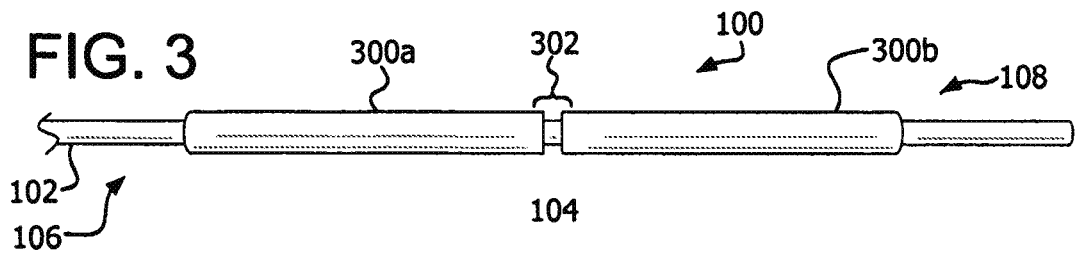
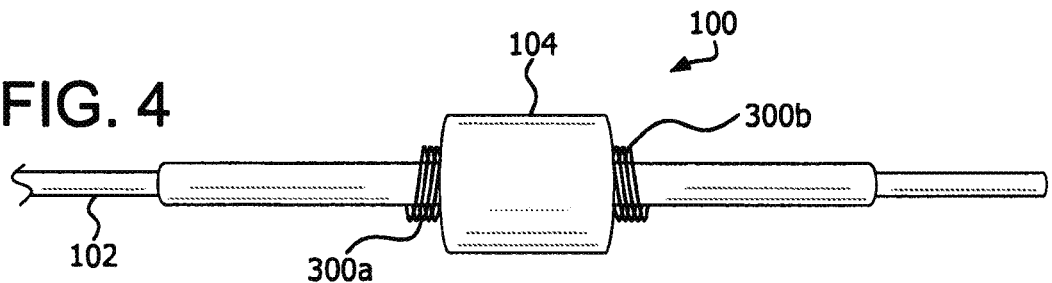
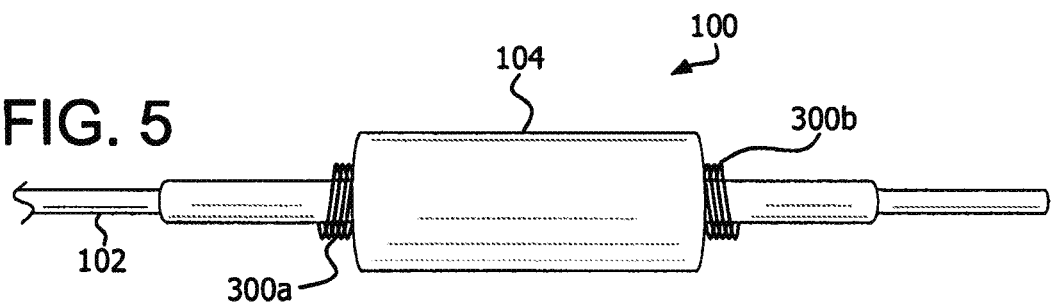
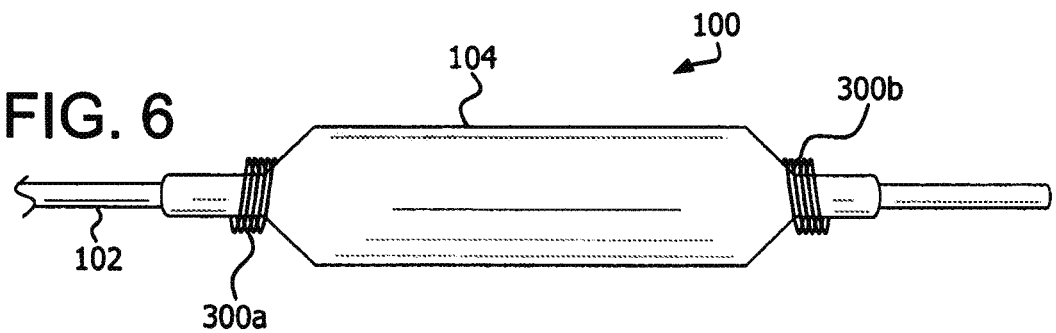
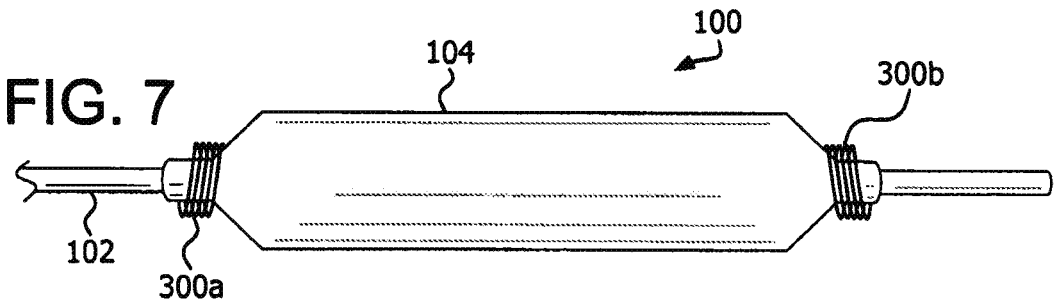

EXPANDABLE MEDICAL DEVICES

BACKGROUND OF THE INVENTION

Vascular dilatation balloons on medical devices generally fall into two classes. The first class of vascular dilatation balloons comprises a noncompliant balloon formed from a relatively nondistensible material such as polyethylene terephthalate (PET). Noncompliant balloons exhibit a substantially uniform exterior inflated profile which remains substantially unchanged upon increasing inflation pressures. Noncompliant balloons have been suggested to be advantageous because they allow the introduction of increased inflation pressure to break calcified lesions while retaining a predictable inflation profile thus minimizing damage to the surrounding lumen. Non-limiting examples of noncompliant balloons are disclosed in U.S. Pat. No. 6,200,290 to Burgmeier and Published Application U.S. 2010/0022949 to Eidenschink. Additional examples are commonly known in the art.

The second class of vascular dilatation balloons comprises compliant balloons. Compliant balloons expand in diameter upon increased inflation pressure. A problem with compliant balloons has been that upon inflation within a lesion, the balloon inflates unevenly around the plaque to form an hour glass type shape. The uneven inflation of the compliant balloon can result in damage to the lumen as well as failure to alleviate the stenosis. Non-limiting examples of compliant balloons are disclosed in U.S. Pat. No. 6,120,477 to Campbell et al. and U.S. Pat. No. 6,890,395 to Simhambhatla, each of which is incorporated by reference herein in its entirety. Additional examples are commonly known in the art.

It is not uncommon with either types of balloons to have some difficulty in properly positioning the balloon, which are usually located on the distal ends of catheters, within the region of the lesion of a patient's artery or other body lumen or, if properly positioned within the lesion, to have difficulty in maintaining the position of the inflatable member or balloon within the lesion during balloon inflation.

What is needed is a balloon which can be preferentially inflated in different sections to better control the position of the balloon and to provide a more uniform pressure against the lesion during the dilatation. In addition, there is a need for a balloon that can be preferentially inflated in different sections to more precisely expand an interventional device at the site of a lesion. Although U.S. Pat. No. 5,470,313 and U.S. Pat. No. 5,843,116 disclose focalized intraluminal balloons with variable inflation zones or regions, the present invention allows any type of balloon to be preferentially inflated at different sections without modifying the balloon or delivery catheter.

SUMMARY OF THE INVENTION

An aspect of the present invention relates to a medical device comprising an elongated tubular body with a proximal control end and distal functional end, at least one expandable element with a middle region, a proximal end and a distal end positioned at the distal functional end of the elongated tubular body, and a slidable constraint surrounding the expandable element. A slidable constraint can comprise at least two portions, each surrounding a section of the expandable element. Upon expansion of the expandable element, the portions of the slidable constraint slide away from the middle region of the expandable element in opposing directions toward the distal end or proximal end of the expandable element so that in the fully expanded state, one portion of the slidable constraint is compressed at the distal end of the expandable element and the other portion of the slidable constraint is compressed at the proximal end of the expandable element. In an alternate embodiment, a slidable constraint can comprise one portion that surrounds an expandable element. An outer protective cover can be placed over the balloon and slidable constraints. This protective cover isolates the sliding film tubes from an overlying stent or from the vasculature wall.

Another aspect of the present invention relates to a method of treating a site in a body lumen. The method comprises providing a medical device comprising an elongated tubular body with a proximal control end and distal functional end, at least one expandable element with a middle region, a proximal end and a distal end positioned at the distal functional end of the elongated tubular body, and a slidable constraint surrounding the expandable element. The slidable constraint comprises at least two portions each surrounding a section of the expandable element. Upon expansion of the expandable element, the portions of the slidable constraint slide in opposing directions away from the middle region of the expandable element toward the distal end or proximal end of the expandable element so that in the fully expanded state, one portion of the slidable constraint is compressed at the distal end of the expandable element and the other portion of the slidable constraint is compressed at the proximal end of the expandable element. In this method, the medical device is positioned within a body lumen so that the expandable element in folded form is adjacent to a treatment site. The expandable element is then expanded at a pressure or force sufficient to expand the expandable element. As the volume of the expansion media is increased (within the expandable element) the working length of the expandable element is increased. Therefore the working length of the expandable element can be adjusted in-situ.

The operation of the present invention should become apparent from the following description when considered in conjunction with the accompanying drawings.

BRIEF DESCRIPTION OF THE FIGURES

FIG. 1 is a schematic illustration of an expandable element in expanded form of a medical device of the present invention.

FIG. 2 is a schematic illustration of an expandable element in folded form of a medical device of the present invention.

FIG. 3 is a schematic illustration of a medical device of the present invention with the expandable element in folded form and a slidable constraint of two portions each surrounding a section of the expandable element.

FIG. 4 is schematic illustration of a medical device of the present invention inflated to a level at which the slidable constraint remains surrounding the expandable element.

FIG. 5 is a schematic illustration of medical device of the present invention inflated at a level greater than depicted in FIG. 4. The portions of the slidable constraint begin sliding away from the middle region of the expandable element in opposing directions toward the distal end or proximal end of the expandable element and so that a portion of the middle region of the expandable element is no longer surrounded by the slidable constraint.

FIG. 6 is a schematic illustration of medical device of the present invention inflated at a level greater than depicted in FIG. 5 so that the portions of the slidable constraint continue sliding away from the middle region of the expandable element in opposing directions toward the distal end and proximal end of the expandable element. A greater portion of the middle region of the expandable element is no longer surrounded by the slidable constraint.

FIG. 7 is a schematic illustration of a medical device of the present invention in a fully inflated state. At this state of full inflation of the expandable element, the portions of the slidable constraint have slid in opposing directions away from the middle region of the expandable element toward the distal end and proximal end of the expandable element so that one portion of the slidable constraint is compressed at the distal end of the expandable element and the other portion of the slidable constraint is compressed at the proximal end of the expandable element.

DETAILED DESCRIPTION OF THE INVENTION

Figure 8:
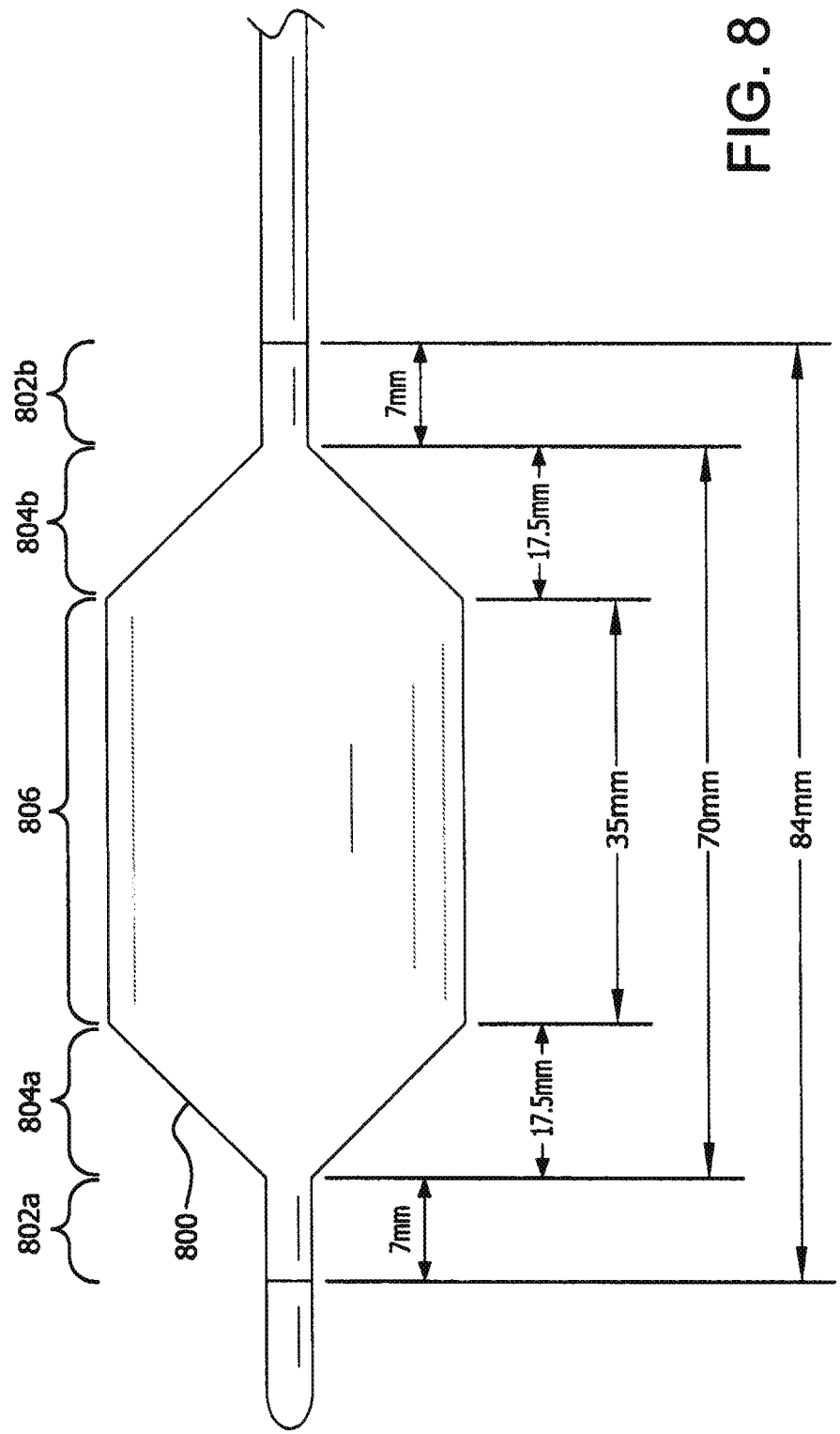
FIG. 8 is a schematic of a side view of an expanded balloon showing typical dimensions.

The present invention relates to medical devices with an expandable portion for insertion into the body lumen. More particularly, the present invention relates to balloon dilatation catheters for insertion in the vascular system.

Medical devices of the present invention comprise an elongated tubular body with a proximal and distal end, at least one expandable element at the distal end of the elongated tubular body, and an expandable tubular sleeve surrounding at least a portion of the expandable element that slides as the expandable element expands. In another embodiment, the balloon dilatation catheter is a focal balloon dilatation catheter, meaning that expansive energy of the balloon is focused at one or more predetermined regions along the surface of the balloon.

Another embodiment of the invention comprises a medical device comprising an elongated tubular body with a proximal control end and a distal functional end, at least one expandable element having a middle region, a distal end and a proximal end, said expandable element positioned at the distal functional end of the elongated tubular body, and a slidable constraint having at least two portions each surrounding at least a section of the expandable element so that upon expansion (e.g. inflation) of the expandable element the at least two portions of the slidable constraint slide in opposing directions away from the middle region toward the distal end and the proximal end of the expandable element. In another embodiment, at least two portions of the slidable constraint are compressed at the distal end and the proximal end of the expandable element when the expandable element is fully expanded. In another embodiment, a portion of the slidable constraint is affixed to the expandable element. In another embodiment, the portion of the slidable constraint is affixed to the expandable element at the distal end. In another embodiment, the portion of the slidable constraint is affixed to the expandable element at the proximal end. In another embodiment, the at least two portions of the slidable constraint are affixed to the expandable element.

In another embodiment, the present invention comprises a catheter, a slidable constraint, and an expandable member for expanding an interventional device, said expandable member preferentially expanded at different sections to better control the expansion of said implantable medical device. Non-limiting examples of said interventional devices are stents (which include stent-grafts) and heart valves. For example, stents that are easily longitudinally compressed during expansion can be expanded by the balloon and cover of the present invention. Said stent can be expanded from the center out, thus maintaining the stent longitudinally tensioned as it is expanded. An example of such a stent is described in U.S. Patent Application Publication 2009/0182413, incorporated by reference herein for all purposes. The longitudinal tension prevents the stent from being longitudinally compressed. Additionally, a heart valve stent may require a stent that should be expanded in a specific shape, wherein the shape is developed in a specific expansion sequence. In other applications, the expansion can begin at one end and progress to the opposing end of the expansible element, thereby creating a "pushing" or peristaltic motion. In one embodiment, said stents can comprise 316L stainless steel, cobalt-chromium-nickel-molybdenum-iron alloy ("cobalt-chromium"), other cobalt alloys such as L605, tantalum, nitinol, or other bio-compatible metals. In another embodiment, the stent can be a self expanding stent, a balloon expandable stent or a combination thereof.

Examples of synthetic polymers suitable for forming a slidable constraint include, but are not limited to nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a slidable constraint material. In one embodiment, said slidable constraint is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. In another embodiment, said slidable constraint comprises expanded fluorocarbon polymers (especially PTFE) materials described in British. Pat. Nos. 1,355,373; 1,506,432; or 1,506,432 or in U.S. Pat. Nos. 3,953,566; 4,187,390; or 5,276,276, the entireties of which are incorporated by reference. Included in the class of preferred fluoropolymers are polytetrafluoroethylene (PTFE), fluorinated ethylene propylene (FEP), copolymers of tetrafluoroethylene (TFE) and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its biocompatibility and its inherent lubricious quality, is ePTFE. In another embodiment, said slidable constraint comprises a combination of said materials listed above. In another embodiment, said slidable constraint is substantially impermeable to bodily fluids. Said substantially impermeable slidable constraint can be made from materials that are substantially impermeable to bodily fluids or can be constructed from permeable materials treated or manufactured to be substantially impermeable to bodily fluids (e.g. by layering different types of materials described above or known in the art).

In one embodiment of the invention, the slidable constraint comprises a polymer. In another embodiment, the material is expanded polytetrafluoroethylene. In another embodiment, the material is ultra high molecular weight polyethylene. In another embodiment, the material is fibrillated.

In another embodiment of the invention, the slidable constraint can comprise differing thicknesses along its longitudinal axis so that as the covers moves (or scrunches) toward the edges, there is an increase the resistance. In effect, this will increase the pressure needed to continue to expand the expandable element. Thus, in another embodiment, the at least two portions of the slidable constraint influence rate of expansion of the expandable element. In another embodiment, the at least two portions of the slidable constraint influence shape of the expandable element upon expansion. In another embodiment, the at least two portions of the slidable constraint influence shape of the expandable element upon expansion. In another embodiment, the at least two portions of the slidable constraint influence amount of force required to expand the expandable element.

As depicted in FIG. 1, in one embodiment, one or more of the portions of the slidable constraint are affixed to the expandable element 104 or to the underlying tubular body 102 using methods commonly known in the art. The slidable constraint may be attached to the tubular body 102 or to the expandable element 104 by various bonding means known to the skilled artisan. Examples include, but are not limited to, solvent bonding, thermal adhesive bonding and heat shrinking or sealing. The selection of the bonding technique is dependent upon the materials from which the expandable element and tubular body are prepared. Refer to U.S. Pat. No. 7,048,713 to Wang, which is incorporated by reference herein in its entirety, for general teachings relating to the attachment of the slidable constraint.

In another embodiment of the invention, the slidable constraint is a single tube with a means of permitting tearing in specific locations along the said cover so that as the expandable member expands said cover will tear at the specific location. The location can be at any location along the longitudinal axis of the slidable constraint. Once the cover tears at a specific location, both sides of the cover will slide away from each other as the expandable member increases in size. In one embodiment, said means comprise perforations being generally oriented circumferentially around the tubular cover. In another embodiment, said means comprise weakened areas of material that will tear circumferentially.

In one embodiment of the invention, the expandable element is a balloon. In another embodiment, said balloon is a compliant or noncompliant balloon. In another embodiment, the expandable element is self-expanding. In another embodiment, the expandable element is mechanically expanded. In another embodiment, wherein the expandable element has a uniform thickness.

A balloon, according to the present invention, may be formed from any materials known to those of skill in the art. Commonly employed materials include the thermoplastic elastomeric and non-elastomeric polymers and the thermosets including the moisture curable polymers.

Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and combinations thereof. Some of these classes are available both as thermosets and as thermoplastic polymers. See U.S. Pat. No. 5,500,181, for example. As used herein, the term copolymer shall be used to refer to any polymeric material formed from more than one monomer.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials which can be employed in balloon formation are described, for example, in U.S. Pat. Nos. 6,406,457; 6,284,333; 6,171,278; 6,146,356; 5,951,941; 5,830,182; 5,556,383; 5,447,497; 5,403,340; 5,348,538; and 5,330,428.

The above materials are intended for illustrative purposes only, and not as a limitation on the scope of the present invention. Suitable polymeric materials available for use are vast and too numerous to be listed herein and are known to those of ordinary skill in the art.

Balloon formation may be carried out in any conventional manner using known extrusion, injection molding and other molding techniques. Typically, there are three major steps in the process which include extruding a tubular preform, molding the balloon and annealing the balloon. Depending on the balloon material employed, the preform may be axially stretched before it is blown. Techniques for balloon formation are described in U.S. Pat. No. 4,490,421, RE32, 983, RE33,561 and U.S. Pat. No. 5,348,538.

The expandable element may be attached to the tubular body by various bonding means known to the skilled artisan.

Examples include, but are not limited to, solvent bonding, thermal adhesive bonding and heat shrinking or sealing. The selection of the bonding technique is dependent upon the materials from which the expandable element and tubular body are prepared. Refer to U.S. Pat. No. 7,048,713 to Wang, which is incorporated by reference herein in its entirety, for general, teachings relating to the bonding of a balloon to a catheter.

In another embodiment, a tubular cover is placed over the balloon and said slidable constraint. This additional cover allows the slidable constraint to slide without interfering with either the vessel and/or an interventional device mounted on the medical device of the invention. Said tubular cover is constructed by methods known in the art, e.g. extrusion, and will depend on the materials used to make said tubular cover. Said tubular cover can be made from any material disclosed herein and known in the art. In another embodiment, said covers can be reinforced to help prevent said expandable element from over expansion. In another embodiment, said tubular cover expands and recovers. This is useful, inter alia, so that the expandable member within the cover can be constrained.

In another embodiment of the invention, said tubular cover and/or slidable constraint can be manufactured from materials that may be impregnated, filled, imbibed or coated with at least one chemical compound known to deliver clinical benefits, for example, chemical compounds that cause a bioactive response. Compounds that cause a bioactive response comprise anti-microbials (e.g. anti-bacterials and anti-virals), anti-inflammatories (e.g. dexamethasone and prednisone), anti-proliferatives (e.g. taxol, paclitaxel and docetaxel) and anti-coagulating agents (e.g. heparin, abciximab, eptifibatide and tirofibran). In one embodiment, said anti-inflammatory is a steroid. In another embodiment, said steroid is dexamethasone. Said tubular cover and/or slidable constraint can also be impregnated, filled, imbibed or coated radio-opaque elements to foster visualization during implantation and/or extraction and/or with materials which "lubricate" the cover, thus allowing the material to slide smoothly across the expandable element and/or tubular cover.

It may also be desirable to modify the ePTFE used for the present invention by incorporating various additives with said ePTFE. Fillers can be incorporated in ePTFE by known methods, such as the methods taught by U.S. Pat. No. 5,879,794, to Korleski. Additives can also be imbibed into the ePTFE by known methods. Additives can also be coated on the ePTFE by known methods. Suitable additives include, for example, materials in particulate and/or fiber form and can be polymers, adhesives, elastomers, ceramics, metals, metalloids, carbon, and combinations thereof. Particularly useful additives include, for example, radiopaque materials, such as certain metals (e.g. barium alloys) and carbon. The additives can be used in combination with desired adhesive materials when incorporated with the polymer. It may also be desirable to metalize the ePTFE or at least a portion thereof. An additive may be included in the matrix of the polymer itself, or contained within the voids defined by the polymeric structure, or both. Desirable fillers may also include colorants, medicaments, anti-microbials, antivirals, antibiotics, antibacterial agents, anti-inflammatory agents, anti-proliferative agents, anti-coagulating agents, hemostatic agents, analgesics, elastomers and mixtures thereof. Compounds which lubricate an ePTFE cover, thus allowing the material to slide smoothly across another material, can be used to coat, fill, or imbibe the tubular cover and/or slidable constraint. Solid lubricants (i.e. graphite, waxes, silicone), fluid lubricants (i.e. hydrocarbon oils, silicone oils), gels (i.e. hydrogel) or any other biocompatible material known in the art may be used. In one embodiment, said tubular cover and/or slidable constraint is coated, filled or imbibed on only one side. In another embodiment, said tubular cover and/or slidable constraint is coated, filled or imbibed on both sides. In another embodiment, said tubular cover and/or slidable constraint is coated, filled or imbibed on only one side and coated, filled or imbibed one the other side with a different material.

Elements of the medical device of the present invention are depicted in FIGS. 1 through 5.

Specifically, FIGS. 1 and 2 are illustrative of a general balloon catheter 100 having an elongated tubular body 102 with an expandable element 104.

The elongated tubular body 102 has a proximal control end 106 and a distal functional end 108. The balloon catheter also has a proximal guidewire lumen 110 that extends through the length of the elongated tubular body 102 and exits the distal end at a guide wire port 112. The balloon catheter shown is an "Over The Wire" configuration, as commonly known in the art. As an alternate, the catheter could have a mid-guidewire port and therefore have a "Rapid Exchange" configuration, as commonly known in the art. The balloon catheter 100 also incorporates a proximal inflation port 114 that allows fluid communication between the inflation port 114 and the inflatable element 104. The length and inner and outer diameter of the tubular body are selected based upon the desired application of the medical device. For example, in one non-limiting embodiment, wherein the medical device is used in percutaneous transluminal coronary angioplasty, the length of the tubular body typically ranges from about 120 cm to about 140 cm. In this embodiment, the outer diameter of the tubular body ranges from about 0.026 inches to about 0.45 inches. As will be understood by the skilled artisan upon reading this disclosure, the length and/or diameter of the tubular body are in no way limiting and may be routinely modified for various applications of the medical devices of the present invention.

The tubular body generally has a circular cross-sectional configuration. However, triangular and oval cross-sectional configurations can also be used.

The tubular body must have sufficient structural integrity to permit the medical device to be advanced to distal vascular locations without bending or buckling upon insertion. Various techniques are known for manufacturing the tubular bodies. In one embodiment, the tubular body is manufactured by extrusion of a biocompatible polymer.

As shown in FIGS. 1 and 2, at least one expandable element 104 is provided at the distal end of the tubular body. An example of an expandable element useful in the present invention is an inflation balloon. Other forms of expandable elements include, but are not limited to mechanical expanders such as "Chinese Lanterns", expandable bow-arms, rotationally expandable/contractible coil springs, cam-type sliding mechanisms, expandable linkages, expandable collets, polymeric or natural materials that expand when activated and other configurations as commonly known in the art. The expandable element used in the medical device of the present invention may also be self-expanding. In one embodiment, the expandable element has an outer wall of uniform thickness. The wall thickness can range from less than about 0.01 mm to about 5 mm. A typical 3 mm diameter thin walled noncompliant balloon can have a wall thickness of about 0.02 mm.

FIG. 1 shows the expandable element 104 in expanded form while FIG. 2 shows the expandable element 104 in folded form.

As shown in FIGS. 3 through 7, the medical device 100 of the present invention further comprises two slidable constraints 300a and 300b surrounding at least a portion of the expandable element 104. Upon inflation of the expandable element, the slidable constraints 300a and 300b slide in opposing directions away from the middle region 302 of the expandable element 104 toward the distal end 108 and the proximal end 106 of the expandable element 104. In the fully inflated state, slidable constraint 300a is compressed at the proximal end 106 of the expandable element 104 and the slidable constraint 300b is compressed at the distal end 108 of the expandable element 104. As more of the inflation media is injected into the expandable element, the two slidable constraints 300a and 300b are driven further away from the center of the expandable element, thereby affecting the working length of the expandable element. The expandable element also is forced to expand from its center out. Various slidable constraints can be combined to affect the expansion profile and/or shape of the expandable element.

Medical devices of the present invention are useful in treating sites in a body lumen or delivering interventional devices as described above. In one embodiment, the medical device of the present invention is used in an angioplasty procedure. In this method, the medical device of the present invention is percutaneously advanced so that the expandable element in folded form is adjacent to a vascular treatment site. Generally the treatment site is a stenosis caused, for example, by plaque or a thrombus. The expandable element of the medical device is then inflated at a pressure or force sufficient to inflate the expandable element. After the stenosis is compressed to or beyond the native diameter of the lumen, the expandable element is evacuated and the medical device is withdrawn from the body lumen. In another embodiment, said medical devices of the present invention are useful for delivering an interventional device a treatment site.

One embodiment of the invention comprises a method of treating a site in a body lumen, said method comprising the steps of positioning within a body lumen the medical device of the invention so that the expandable element in folded form is adjacent to a treatment site; and inflating the expandable element at a pressure or force sufficient to expand the expandable element and to slide said slidable constraint portions in opposing directions. In one embodiment, said expandable element expands an interventional device. In another embodiment, said interventional device is a stent. In another embodiment, said interventional device is a heart valve. In another embodiment, said treatment site is a coronary artery. In another embodiment, wherein the two portions of the slidable constraint are compressed at the distal end and the proximal end of the expandable element when the expandable element is fully expanded. In another embodiment, a portion of the slidable constraint is affixed to the expandable element. In another embodiment, the portion of the slidable constraint is affixed to the expandable element at the distal end. In another embodiment, the portion of the slidable constraint is affixed to the expandable element at the proximal end. In another embodiment, the at least two portions of the slidable constraint are affixed to the expandable element. In another embodiment, the expandable element is a balloon. In another embodiment, said slidable constrain comprises at least one polymer. In another embodiment, said polymer is expanded polytetrafluoroethylene. In another embodiment, the at least two portions of the slidable constraint influence rate of expansion of the expandable element. In another embodiment, the at least two portions of the slidable constraint influence shape of the expandable element upon inflation. In another embodiment, the at least two portions of the slidable constraint influence amount of force required to expand the expandable element.

The following non-limiting examples are provided to further illustrate the present invention.

Example 1

Two non-expandable film tubes were attached to the ends of a balloon so that when the balloon was expanded, the two film tubes were "pushed-off" the balloon. The balloon therefore expanded from the middle out. An outer protective cover was placed over the balloon/film tubes. This protective cover isolates the sliding film tubes from an overlying stent or from the vasculature wall. The following example details a method of making such a balloon assembly.

A folded and compressed PET balloon catheter assembly was provided. The balloon had a total length from the first cone to the second cone of about 70 mm, a working length of about 35 mm, and a compressed diameter of about 3.8 mm. The PET balloon first taper had a length of about 17.5 mm. The PET balloon second taper had a length of about 17.5 mm. The PET balloon first leg had a length of about 7 mm. The PET balloon second leg had a length of about 7 mm. The balloon is shown in side view FIG. 8. Shown is an inflated balloon 800 having opposed leg portions 802a and 802b, opposed tapered portions 804a and 804b and a center body portion 806. Typical dimensions of the legs, tapered portions and body are also shown. The inflated balloon had an outer diameter of about 28 mm.

To make the slidable constraints, an ePTFE film was helically wrapped onto a mandrel having a diameter of about 4 mm and a length of about 37 cm. The film had a width of about 2.54 cm and wrapped with a pitch of about 2.794 mm (measured from adjacent film edges). Two passes of film were wrapped, using a 2.794 mm pitch (measured from adjacent film edges) with a film angle of about 78°. The wrapped length was about 30 cm. The film wrapped mandrel was the placed into an air convection oven heated to about 380° C. for about 28 minutes. This heat exposure bonded the layers of ePTFE, forming a thin film tube. The ePTFE film wrapped mandrel was removed from the oven, allowed to cool, and the thin film tube was removed from the mandrel. The thin film tube had a length of about 30 cm, a diameter of about 4 mm, and a wall thickness of about 0.0381 mm.

Two about 47 mm lengths of thin film tube were cut from the about 30 cm length of thin film tube. A first 47 mm length of thin film tube was then placed over the leg, taper and a portion of the working length of the end of the compacted PET balloon nearest to the catheter hub. One end of the film tube was aligned to the center of the balloon body. The end of the thin film tube placed over the balloon leg was then secured to the balloon leg with Loctite Cyanoacrylate adhesive (Loctite Cyanoacrylate adhesive #4981) and 0.635 cm ePTFE film wrapped around both the thin film tube and balloon leg. A second about 47 mm length of thin film tube was then placed over the leg, taper and a portion of the working length of the end of the compacted PET balloon nearest to the leading tip of the balloon catheter. One end of the film tube was abutted against the first film tube so that the two tube ends were positioned about the center of the balloon body. The end of the thin film tube placed over the balloon leg was then secured to the balloon leg with Loctite Cyanoacrylate adhesive and 0.635 cm ePTFE film wrapped around both the thin film tube and the balloon leg.

A third ePTFE thin film tube was placed over the balloon/film tubes. This third protective cover isolates the sliding film tubes from an overlying stent or from the vasculature wall. This third film tube expands along with the balloon.

To make the third film tube, an ePTFE film was helically wrapped around a mandrel having a diameter of about 28.5 mm and a length of about 37 cm. The film width was about 2.54 cm. Two passes of film were wrapped in opposing directions, using a 2.794 mm pitch (measured from adjacent film edges) with a film angle of about 78°. The wrapped length was about 30 cm. The film wrapped mandrel was then placed into an air convection oven heated to about 380° C. for about 28 minutes. This heat exposure bonded the layers of ePTFE, forming a thin film tube. The ePTFE film wrapped mandrel was removed from the oven, allowed to cool, and the thin film tube was removed from the mandrel. The thin film tube had a diameter of about 28.5 mm and a wall thickness of about 0.0254 mm. The about 30 cm long thin film tube and was then tensioned by hand and stretched longitudinally to about 400% of the original length, or to about 120 cm. After stretching, the tube was placed onto a mandrel having a diameter of about 4 mm and a length of about 130 cm. The stretched tube was smoothed by hand onto the mandrel, forming a small diameter thin film tube having a diameter of about 4 mm. A temporary ePTFE film was then helically wrapped onto the about 4 mm diameter thin wall tube. The film thickness was about 0.00508 mm and the film width was about 1.905 cm. One pass of film was wrapped, using a 2.6924 mm pitch (measured from adjacent film edges) with a film angle of about 78°. The thin film tube and temporary ePTFE film wrap was then longitudinally compressed to about 50% of its original length. The thin film tube had an initial length of about 120 cm and was compressed to a length of about 60 cm. The longitudinally compressed thin film tube and mandrel was then placed into an air convection oven heated to about 380° C. for about 1 minute. The ePTFE film wrapped mandrel was then removed from the oven and allowed to cool. The temporary ePTFE film wrap was then removed from the thin film tube. An about 80 mm length of the thin film tube was cut from the about 60 cm length of thin film tube.

The thin film tube was then placed over the PET balloon and ePTFE thin film tube assembly, as described above. The ends of the thin film tube were secured to the catheter using a Loctite Cyanoacrylate adhesive and 0.635 cm wide ePTFE film wrapped around both the thin film tube and the catheter.

A first pressure of about 4 atm applied to the balloon catheter inflated the middle portion of the balloon. As the balloon inflated the two 4 mm (47 mm long) thin film tubes were pushed away from the balloon center, allowing the center of the balloon to inflate to the nominal diameter. As further inflation media was injected, the two 4 mm thin film tubes were further forced away from the balloon center. As further inflation media was injected, the inflated region of the PET balloon extended in length until the balloon was fully extended. The inflation sequence is depicted in FIGS. 3-7. The third thin film protective cover is not shown for clarity.

Example 2

A non-expandable film tube having a central "rip point" was attached to the ends of a balloon. When the balloon was expanded, the film tube split and the two tube portions were "pushed-off" the balloon. The balloon therefore expanded from the middle out. An outer protective cover was placed over the balloon/film tubes. The following example details a method of making such a balloon assembly.

A folded and compressed PET balloon catheter assembly, as describe in Example 1, was provided.

To make the slidable constrain, an ePTFE film was helically wrapped onto a mandrel having a diameter of about 4 mm and a length of about 37 cm. The film had a width of about 2.54 cm and wrapped with a pitch of about 2.794 mm (measured from adjacent film edges). Two passes of film were wrapped, using a 2.794 mm pitch (measured from adjacent film edges) with a film angle of about 78°. The wrapped length was about 30 cm.

The film wrapped mandrel was the placed into an air convection oven heated to about 380° C. for about 28 minutes. This heat exposure bonded the layers of ePTFE, forming a thin film tube.

The ePTFE film wrapped mandrel was removed from the oven, allowed to cool, and the thin film tube was removed from the mandrel. The thin film tube had a length of about 30 cm, a diameter of about 4 mm, and a wall thickness of about 0.0381 mm.

Figure 9:
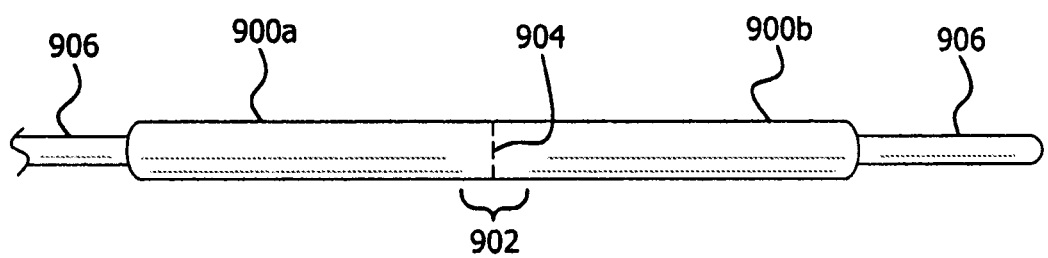
FIG. 9 is a schematic illustration of a film tube having two portions and joined by a perforated center section. The perforated thin film tube was placed over the balloon and secured to the balloon legs.

A 120 mm length of thin film tube was cut from the about 30 cm length of thin film tube. The 120 mm length was then placed onto a mandrel having a diameter of about 4 mm. The mandrel was then fixed onto a laser and a series of perforations were cut circumferentially about the center of the tube. The perforations were about 0.5 mm in diameter and were spaced about 0.7 mm center to center. The perforated film tube is shown in side view FIG. 9. Shown in FIG. 9 is a film tube having two portions 900*a* and 900*b* joined by a perforated center section 902 that has a series of perforations 904. The film tube is shown mounted onto a mandrel 906. The perforated thin film tube was placed over the balloon and secured to the balloon legs with 4981 Loctite Cyanoacrylate adhesive and 0.635 cm ePTFE film wrapped around both the thin film tube and balloon leg.

A third ePTFE thin film tube, made as describe above, was placed over the balloon/film tubes. The ends of the thin film tube were secured to the catheter using Loctite Cyanoacrylate and 0.635 cm wide ePTFE film wrapped around both the thin film tube and the catheter.

A first pressure of about 4 atm applied to the balloon catheter, describe in this Example, inflated the middle portion of the balloon, causing the 4 mm inner film tube to split apart along the circumferential perforations, forming two inner tubes. As the balloon inflated the two 4 mm thin film tubes were pushed away from the balloon center, allowing the center of the balloon to inflate to the nominal diameter. As further inflation media was injected, the two 4 mm thin film tubes were further forced away from the balloon center. As further inflation media was injected, the inflated region of the PET balloon extended in length until the balloon was fully extended. The inflation sequence is depicted in FIGS. 3-7. The third thin film protective cover is not shown for clarity.

Example 3

A single non-expandable film tube was attached to an end of a balloon so that when the balloon was expanded, the film tube was "pushed-off" the balloon. The balloon therefore expanded from one end out. An outer protective cover was placed over the balloon/film tube. The following example details a method of making such a balloon assembly.

A folded and compressed PET balloon catheter assembly, as describe in Example 1, was provided.

To make the slidable constraint, an ePTFE film was helically wrapped onto a mandrel having a diameter of about 4 mm and a length of about 37 cm. The film had a width of about 2.54 cm and wrapped with a pitch of about 2.794 mm (measured from adjacent film edges). Two passes of film were wrapped, using a 2.794 mm pitch (measured from adjacent film edges) with a film angle of about 78°. The wrapped length was about 30 cm.

The film wrapped mandrel was the placed into an air convection oven heated to about 380° C. for about 28 minutes. This heat exposure bonded the layers of ePTFE, forming a thin film tube.

The ePTFE film wrapped mandrel was removed from the oven, allowed to cool, and the thin film tube was removed from the mandrel. The thin film tube had a length of about 30 cm, a diameter of about 4 mm, and a wall thickness of about 0.0381 mm.

A 47 mm length of thin film tube was cut from the about 30 cm length of thin film tube. The 47 mm length film tube was placed over the balloon with one end of the film tube aligned to the center of the balloon body. The opposing end of the film tube was secured to the balloon leg with Loctite Cyanoacrylate adhesive and 0.635 cm ePTFE film wrapped around both the thin film tube and balloon leg.

A third ePTFE thin film tube, made as describe above, was placed over the balloon/film tubes. The ends of the thin film tube were secured to the catheter using Loctite Cyanoacrylate adhesive and 0.635 cm wide ePTFE film wrapped around both the thin film tube and the catheter.

The thin film tube was then placed over the PET balloon and the ePTFE thin film tube assembly described in this Example. The ends of the thin film tube were secured to the catheter using Loctite Cyanoacrylate adhesive and 0.635 cm wide ePTFE film wrapped around both the thin film tube and the catheter.

Figure 10:
FIGS. 10 to 13 are a schematic illustration of a compacted balloon attached to an elongated catheter shaft. A portion of the compacted balloon is covered by a film tube. As the balloon inflates, the film tube is progressively pushed off the balloon.
Figure 11:
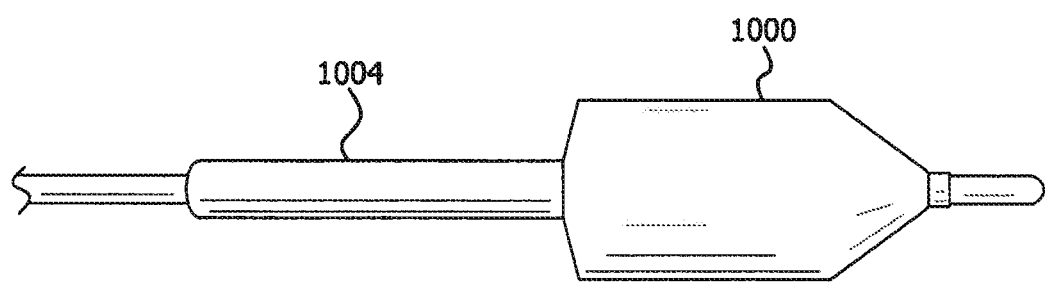
Figure 12:
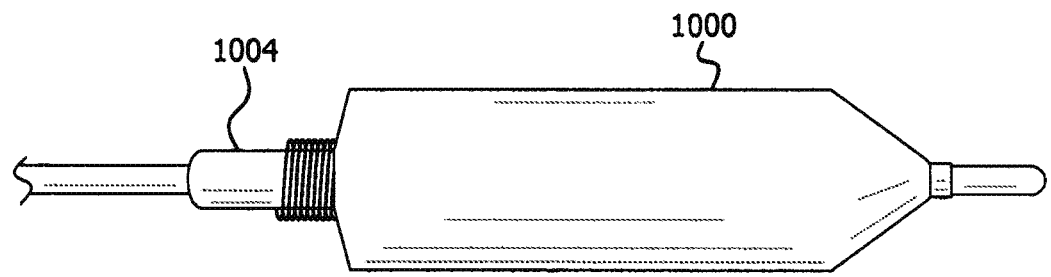
Figure 13:
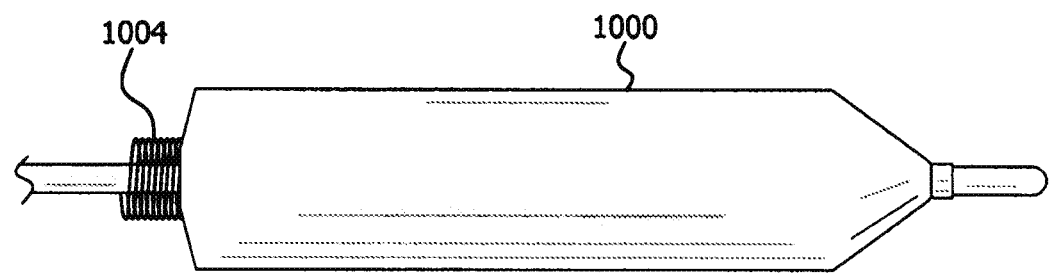

A first pressure of about 2 atm applied to the balloon catheter, described in this Example, inflated the first half of the balloon. As additional inflation media was injected, the balloon pushed the film tube away from the balloon center. As the balloon was further inflated the 4 mm thin film tube was further pushed away from the balloon center, allowing the balloon to inflate to the nominal diameter. The inflation sequence is depicted in FIGS. 10-13. The third thin film protective cover is not shown for clarity. Shown in FIG. 10 is a compacted balloon 1000 attached to an elongated catheter shaft 1002. A portion of the compacted balloon is covered by a film tube 1004. As shown in FIGS. 11-13, as the balloon 1000 inflated, the film tube 1004 was progressively pushed off the balloon.

Example 4

Non-expandable film tubes were attached to the balloon ends so that when expanded the balloon "pushed-off" the film tubes. The film tubes were dimensioned to leave a 25 mm long center section of the balloon uncovered. The 25 mm center of the balloon fully expanded at a first pressure and then fully expanded as more inflation media was injected. An outer protective cover was placed over the balloon/film tubes. The following example details a method of making such a balloon assembly.

A folded and compressed PET balloon catheter assembly, as describe in Example 1, was provided.

To make the slidable constraints, an ePTFE film was helically wrapped onto a mandrel having a diameter of about 4 mm and a length of about 37 cm. The film had a width of about 2.54 cm and wrapped with a pitch of about 2.794 mm (measured from adjacent film edges). Two passes of film were wrapped, using a 2.794 mm pitch (measured from adjacent film edges) with a film angle of about 78°. The wrapped length was about 30 cm.

The film wrapped mandrel was the placed into an air convection oven heated to about 380° C. for about 28 minutes. This heat exposure bonded the layers of ePTFE, forming a thin film tube.

The ePTFE film wrapped mandrel was removed from the oven, allowed to cool, and the thin film tube was removed from the mandrel. The thin film tube had a length of about 30 cm, a diameter of about 4 mm, and a wall thickness of about 0.0381 mm.

Two about 35 mm lengths of thin film tube were cut from the about 30 cm length of thin film tube. A first 35 mm length of thin film tube was then placed over the leg, taper and a portion of the working length of the end of the compacted PET balloon nearest to the catheter hub. The end of the thin film tube placed over the balloon leg was then secured to the balloon leg with Loctite Cyanoacrylate adhesive and 0.635 cm ePTFE film wrapped around both the thin film tube and balloon leg. A second about 35 mm length of thin film tube was then placed over the leg, taper and a portion of the working length of the end of the compacted PET balloon nearest to the leading tip of the balloon catheter. The end of the thin film tube placed over the balloon leg was then secured to the balloon leg with Loctite Cyanoacrylate adhesive and 0.635 cm ePTFE film wrapped around both the thin film tube and the balloon leg. The resulting balloon catheter assembly had an about 25 mm length of compacted PET balloon not covered by the first or second ePTFE thin film tube.

A third ePTFE thin film tube, made as describe above, was placed over the balloon/film tubes. The ends of the thin film tube were secured to the catheter using Loctite Cyanoacrylate and 0.635 cm wide ePTFE film wrapped around both the thin film tube and the catheter. The balloon was preconditioned by inflating the balloon. The two ends of the balloon were constrained by the 4 mm tubes, allowing only the 25 mm long middle portion of the balloon to inflate.

Figure 14:
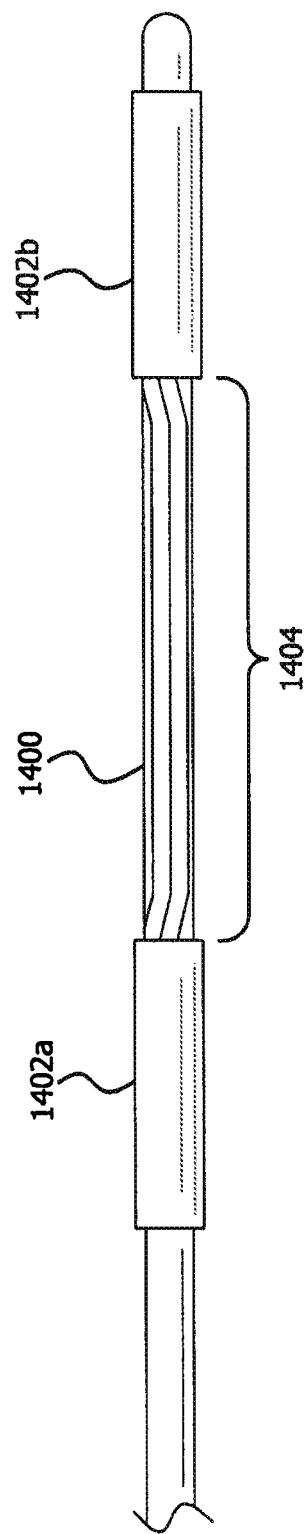
FIG. 14 is a schematic illustration of a compacted balloon partially covered by two film tubes. The two film tubes were positioned onto the balloon leaving a center gap.
Figure 15:
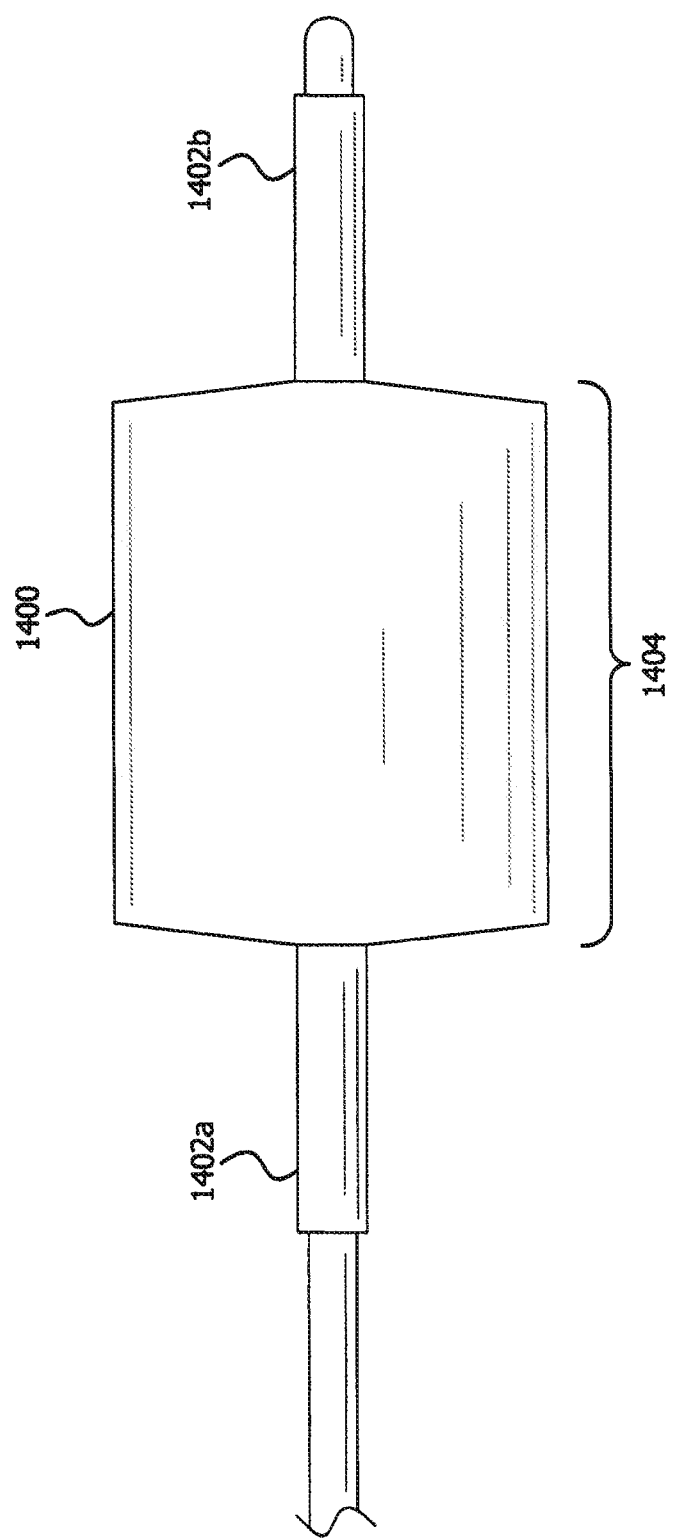
FIG. 15 is a schematic of a first pressure applied to the balloon depicted in FIG. 14. The balloon inflated in the long middle portion of the balloon not covered by the first or second ePTFE thin film tubes.

Shown in FIG. 14 is a compacted balloon 1400 partially covered by two film tubes 1402a and 1402b. The two film tubes were positioned onto the balloon leaving a 25 mm center gap 1404. As shown in FIG. 15, a first pressure of about 2 atm applied to the balloon 1400 inflated the about 25 mm long middle portion 1404 of the balloon not covered by the first or second ePTFE thin film tubes 1402a and 1402b. The inflated middle portion of the balloon attained a diameter of about [28 mm.]

Figure 16:
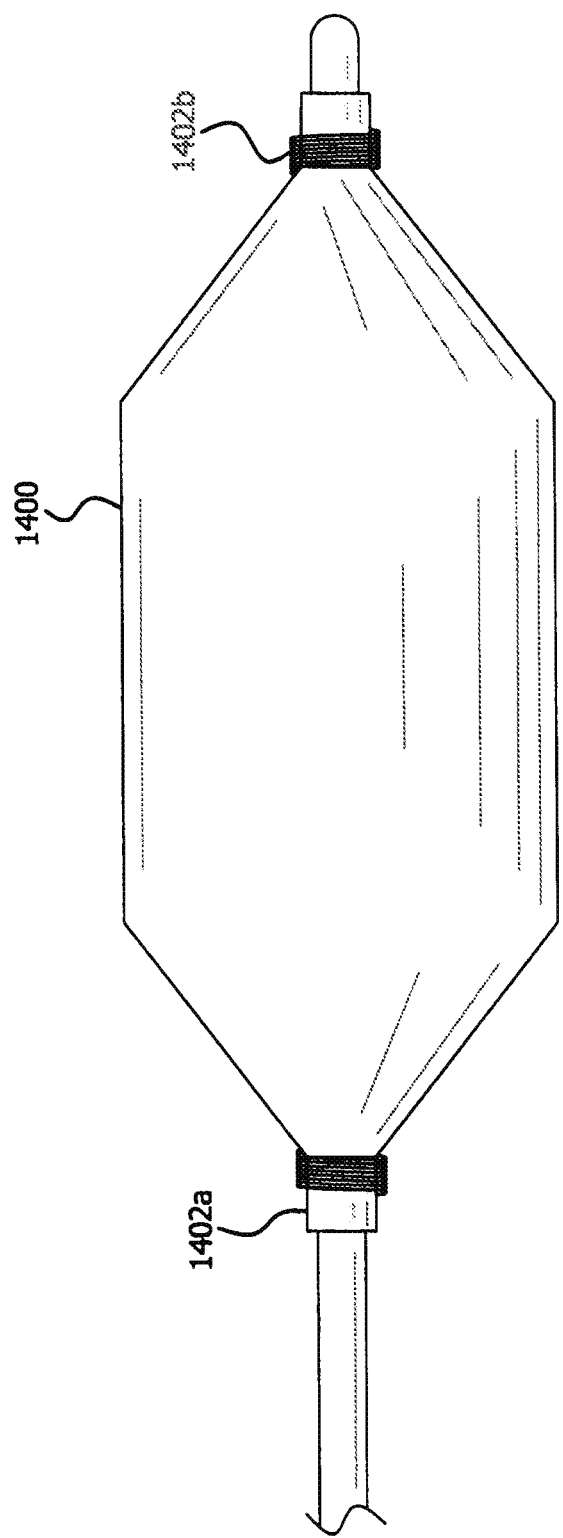
FIG. 16 is a schematic of additional inflation media injected into the balloon of FIGS. 14 and 15, which caused the balloon to "push off" the first and second ePTFE thin film tubes. The inflated region of the balloon extended in length until the balloon was fully extended.

As shown in FIG. 16, additional inflation media injected into the balloon 1400 caused the balloon to "push off" the first and second ePTFE thin film tubes 1402a and 1402b. The inflated region of the PET balloon extended in length until the balloon was fully extended.

The nominal balloon dimensions were achieved as additional inflation media was injected. The inflation sequence is depicted in FIGS. 14-16. The third thin film protective cover is not shown for clarity.

Example 5

Two film tubes were placed over a compacted PET balloon and attached to the balloon ends. The film tubes had discrete zones with different amounts of radial compliance, which was achieved through wrapping the ePTFE film at different diameters. The end of the film tube placed over the middle of the compacted PET balloon is compliant and expanded in diameter up to about 18 mm. The ends of the film tubes had minimal radial compliance and did not increase in diameter substantially above the diameter of the compacted PET balloon. The two film tubes placed over the balloon came in close proximity to each other, essentially touching each other, at the middle of the balloon. The resulting balloon inflated first in the middle zone to about 18 mm in diameter when a first pressure was applied to the balloon. When a second, higher pressure was applied to the balloon, the two film tubes were pushed away from the middle and towards the ends of the balloon, allowing the balloon to inflate to its nominal diameter from the middle out to the edges.

To make the slidable constraints, an ePTFE film was helically wrapped around a mandrel having a diameter of about 18 mm and a length of about 37 cm. The film width was about 2.54 cm. Two passes of film were wrapped in opposing directions, using a 2.794 mm pitch (measured from adjacent film edges) with a film angle of about 78°. The wrapped length was about 30 cm.

The film wrapped mandrel was then placed into an air convection oven heated to about 380° C. for about 28 minutes. This heat exposure bonded the layers of ePTFE, forming a thin film tube.

The ePTFE film wrapped mandrel was removed from the oven, allowed to cool, and the thin film tube was removed from the mandrel. The thin film tube had a diameter of about 18 mm and a wall thickness of about 0.0254 mm.

The about 30 cm long thin film tube was then tensioned by hand and stretched longitudinally to about 400% of the original length, or to about 120 cm. After stretching, the tube was placed onto a stainless steel mandrel having a diameter of about 4 mm and a length of about 130 cm. The stretched tube was smoothed by hand onto the mandrel, forming a small diameter thin film tube having a diameter of about 4 mm.

Two pieces of thin film tube about 47 mm long each were cut from the about 120 cm long thin film tube.

A folded and compressed PET balloon catheter assembly, as described in Example 1 was provided. The two thin film tubes were then secured to the balloon legs with Loctite Cyanoacrylate adhesive and 0.635 mm ePTFE film wrapped around the end of the thin film tube and the balloon leg.

A third ePTFE thin film tube, made as describe above, was placed over the balloon/film tubes. The ends of the thin film tube were secured to the catheter using Loctite Cyanoacrylate adhesive and 0.635 cm wide ePTFE film wrapped around both the thin film tube and catheter.

Figure 17:
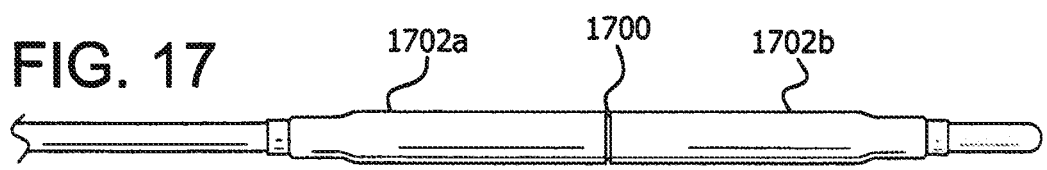
FIGS. 17 to 21 are a schematic illustration of an inflation sequence. In this sequence, the third protective outer tube is not shown for clarity

The inflation sequence is shown in FIGS. 17-21. In this sequence, the third protective outer tube is not shown for clarity. Shown in FIG. 17 is the compacted balloon 1700 with the two film tubes 1702*a* and 1702*b* centered about the center of the balloon body.

Figure 18:
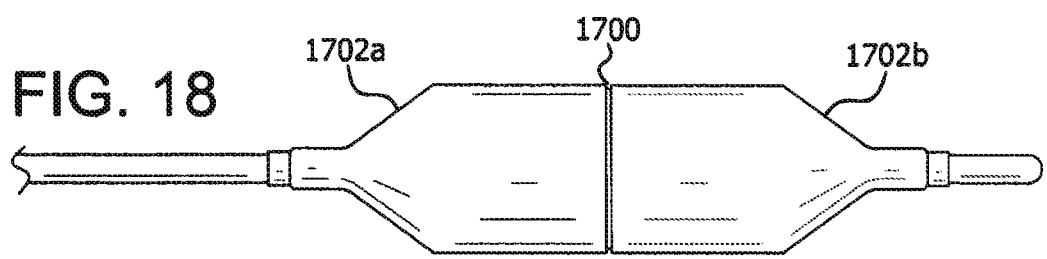

As shown in FIG. 18, a first pressure of about 4 atm was applied to the balloon assembly that caused the entire balloon 1700 (and the two film tubes 1702*a* and 1702*b*) to expand to a first diameter of about 18 mm.

Figure 19:
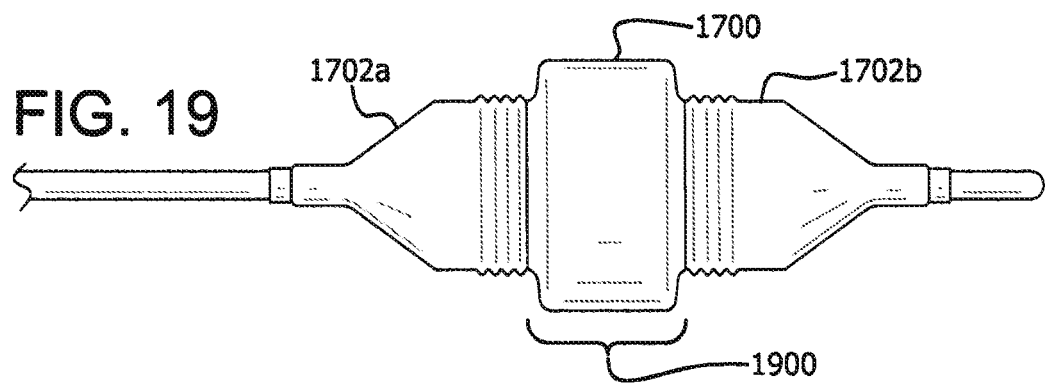

As shown in FIG. 19, a second higher pressure of about 6 atm was applied to the balloon 1700 that caused the center section 1900 of the balloon to expand to a diameter of about 25 mm. As the balloon expanded, the two film tubes 1702*a* and 1702*b* were pushed away from the center of the balloon.

Figure 20:
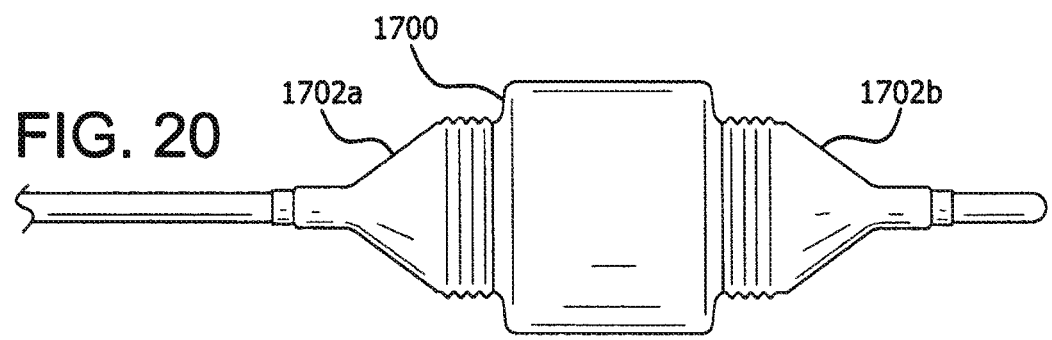
Figure 21:
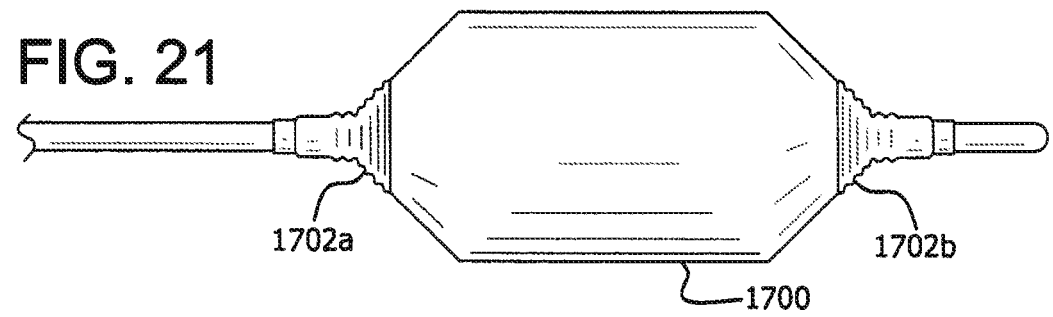
Figure 22:
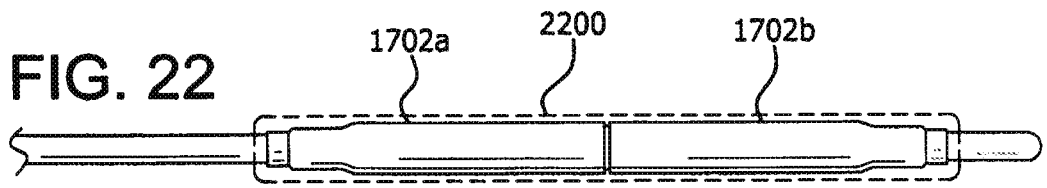
FIGS. 22 to 26 are a schematic illustration of the inflation sequence depicted in FIGS. 17 to 21 showing the third outer protective covering.
Figure 23:
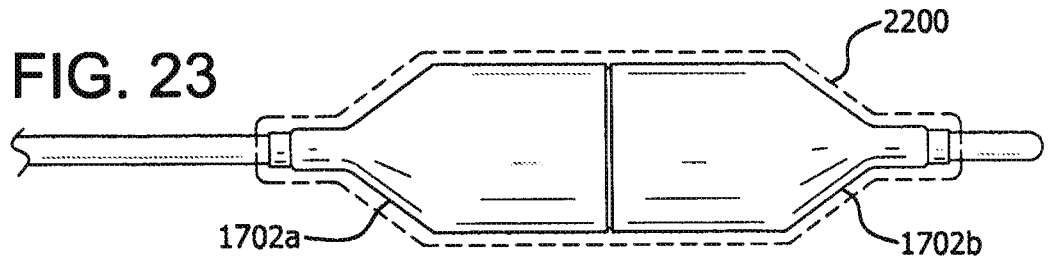
Figure 24:
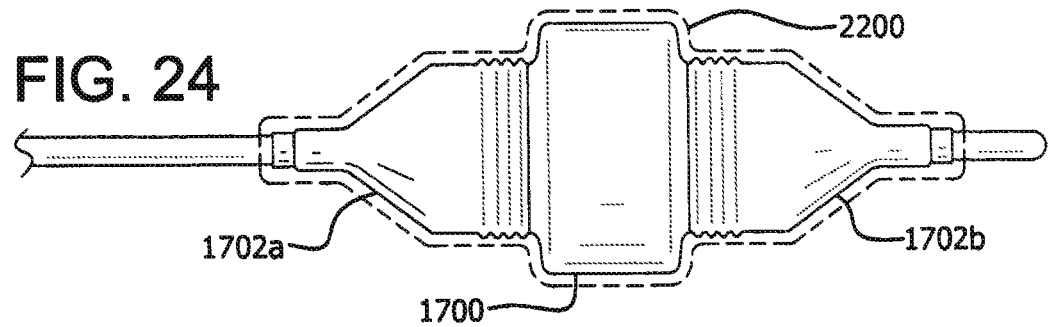
Figure 25:
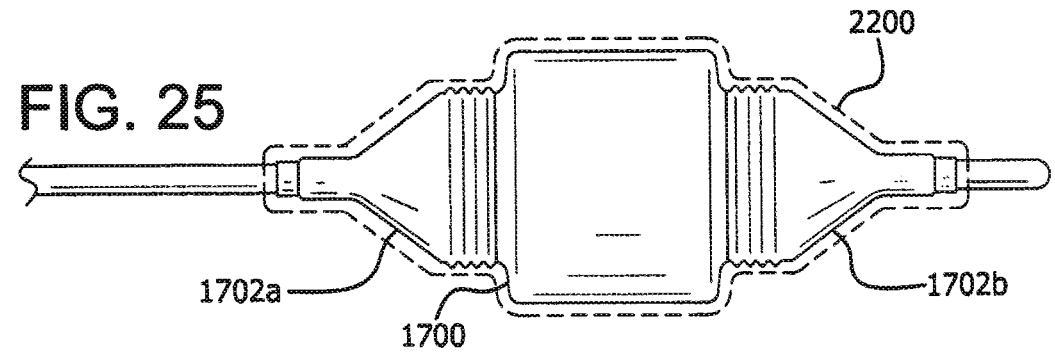
Figure 26:
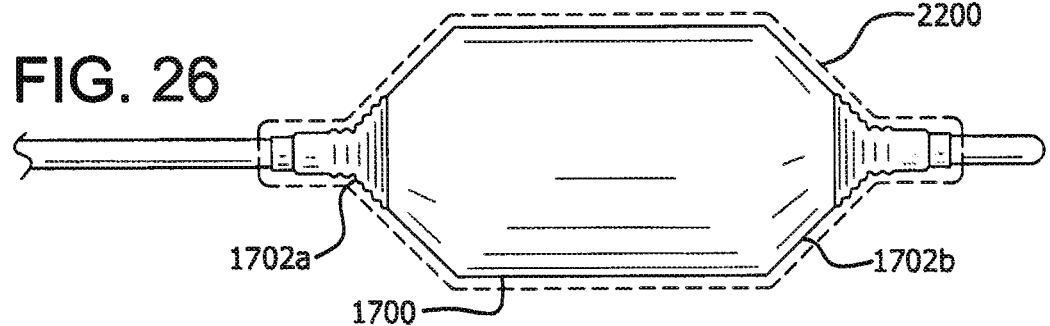

As shown in FIGS. 20 and 21, as additional inflation media was injected into the balloon 1700, the entire balloon expanded to a nominal diameter of about 25 mm and the two film tubes 1702*a* and 1702*b* were forced off onto the balloon legs.

FIGS. 22-26 show an inflation sequence identical to that shown in FIGS. 17-21 with the addition of showing the third outer protective covering 2200.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:
1. A medical device comprising:
   a. an elongated tubular body with a proximal control end and a distal functional end;
   b. a balloon having a working length, a distal end, a proximal end, and a middle region, said balloon positioned at the distal functional end of the elongated tubular body; and
   c. a slidable balloon constraint having at least two portions, the slidable balloon constraint extending along the working length of the balloon, wherein an end of a first portion of the at least two portions and an end of a second portion of the at least two portions are each positioned about the middle region of the balloon so that at least a majority of the balloon working length is covered by the at least two portions,
   wherein in response to a first pressure being applied to the balloon, the balloon and the at least two portions of the slidable balloon constraint expand to a first diameter,
   wherein upon an application of a second pressure greater than the first pressure to the balloon, a length of the working length of the balloon extends beyond the first diameter to a second diameter,
   wherein upon the application of the second pressure the at least two portions of the slidable balloon constraint and a portion of the working length of the balloon surrounded by the at least two portions of the slidable balloon constraint are constrained to a diameter that is less than the second diameter, and
   wherein upon the application of additional inflation media the at least two portions of the slidable balloon constraint retract and slide in opposing directions towards the distal end and the proximal end of the balloon to increase a separation distance between the at least two portions of the slidable balloon constraint to increase the length of the working length of the balloon at the second diameter.

2. The medical device of claim 1, wherein the at least two portions of the slidable balloon constraint are compressed at the distal end and the proximal end of the balloon when the balloon is fully inflated.

3. The medical device of claim 1, wherein one of the at least two portions of the slidable balloon constraint is affixed to the balloon.

4. The medical device of claim 3, wherein the one of the at least two portions of the slidable balloon constraint is affixed to the balloon at the distal end.

5. The medical device of claim 3, wherein the one of the at least two portions of the slidable balloon constraint is affixed to the balloon at the proximal end.

6. The medical device of claim 1, wherein the at least two portions of the slidable balloon constraint are affixed to the balloon.

7. The medical device of claim 1, wherein the balloon has uniform thickness.

8. The medical device of claim 1, wherein the slidable balloon constraint comprises a polymer.

9. The medical device of claim 8, wherein said polymer is expanded polytetrafluoroethylene.

10. The medical device of claim 8, wherein said polymer is ultra high molecular weight polyethylene.

11. The medical device of claim 8, wherein said polymer is fibrillated.

12. The medical device of claim 1, wherein the at least two portions of the slidable balloon constraint influence rate of expansion of the balloon.

13. The medical device of claim 1, wherein the at least two portions of the slidable balloon constraint influence shape of the balloon upon inflation.

14. The medical device of claim 1, wherein the at least two portions of the slidable balloon constraint influence an amount of force required to expand the balloon.

15. A method of treating a site in a body lumen, said method comprising the steps of positioning within a body lumen the medical device of claim 1, so that the balloon in folded form is adjacent to a treatment site; and expanding the balloon at the second pressure, the second pressure being sufficient to expand the balloon and to retract and slide said at least two portions of the slidable balloon constraint in opposing directions to define a portion of the separation distance between the at least two portions of the slidable balloon constraint.

16. The method of claim 15, wherein said balloon expands an interventional device.

17. The method of claim 16, wherein said interventional device is a stent.

18. The method of claim 16, wherein said interventional device is a heart valve.

19. The method of claim 15, wherein said treatment site is a coronary artery.

20. The method of claim 15, wherein the at least two portions of the slidable balloon constraint are compressed at the distal end and the proximal end of the balloon when the balloon is fully inflated.

21. The method of claim 15, wherein at least one of the at least two portions of the slidable balloon constraint is affixed to the balloon.

22. The method of claim 21, wherein at least one of the at least two portions of the slidable balloon constraint is affixed to the balloon at the distal end.

23. The method of claim 21, wherein at least one of the at least two portions of the slidable balloon constraint is affixed to the balloon at the proximal end.

24. The method of claim 15, wherein at least one of the at least two portions of the slidable balloon constraint are affixed to the balloon.

25. The method of claim 15, wherein the slidable balloon constraint comprises a polymer.

26. The method of claim 25, wherein said polymer is expanded polytetrafluoroethylene.

27. The method of claim 15, wherein the at least two portions of the slidable balloon constraint influence a rate of expansion of the balloon.

28. The method of claim 15, wherein the at least two portions of the slidable balloon constraint influence the shape of the balloon upon expansion.

29. The method of claim 15, wherein the at least two portions of the slidable balloon constraint influence an amount of force required to expand the balloon.

30. The method of claim 15, wherein said medical device further comprises an additional cover.

31. The medical device of claim 1, wherein the first portion and the second portion cooperate to cover the entirety of the balloon.

32. The medical device of claim 1, wherein the first portion and the second portion are in contact at the first diameter.

33. The medical device of claim 1, wherein the first portion and the second portion are shortened upon retraction.

* * * * *